United States Patent [19]

Neiheisel et al.

[11] 4,223,346
[45] Sep. 16, 1980

[54] AUTOMATIC DEFECT DETECTING INSPECTION APPARATUS

[75] Inventors: Gary L. Neiheisel, Cincinnati; Bradley R. Hoover, Hamilton, both of Ohio

[73] Assignee: Armco Inc., Middletown, Ohio

[21] Appl. No.: 27,320

[22] Filed: Apr. 5, 1979

[51] Int. Cl.² .................... H04N 5/72; H04N 7/18
[52] U.S. Cl. .................... 358/106; 250/572; 356/237; 356/430; 358/225
[58] Field of Search ............ 358/106, 213, 225; 250/572; 356/430, 237

[56] References Cited

U.S. PATENT DOCUMENTS

| | | | |
|---|---|---|---|
| 2,803,755 | 8/1957 | Milford | 358/106 |
| 3,096,443 | 7/1963 | Laycak | 235/92 R |
| 3,176,306 | 3/1965 | Burns | 250/572 |
| 3,803,353 | 4/1974 | Sanderson | 358/213 |
| 3,877,821 | 4/1975 | Price | 250/563 |
| 4,004,152 | 1/1977 | Obser | 250/572 |
| 4,158,134 | 6/1979 | Martin | 250/578 |

FOREIGN PATENT DOCUMENTS 684601 4/1964 Canada ..................... 250/572

*Primary Examiner*—Howard W. Britton
*Attorney, Agent, or Firm*—Frost & Jacobs

[57] ABSTRACT

Automatic defect detecting inspection apparatus for detecting defects or imperfections contained in or on a moving slab or strip. The defect detection apparatus utilizes a linear light source for illuminating a selected portion of the slab or sheet surface and an array of optically sensitive elements arranged in side-by-side relationship to scan the surface of the sheet or slab in a direction transverse to the direction of movement to produce an output video signals corresponding to the optical intensity of the area scanned. An anamorphic optical system comprising spaced cylindrical lenses forming a Galilean telescope positioned between the moving material and the optically sensitive elements increases the sensitivity of the optically sensitive elements in the direction of the material movement while maintaining the sensitivity of the optical elements substantially unchanged in the direction transverse to the material movement.

8 Claims, 7 Drawing Figures

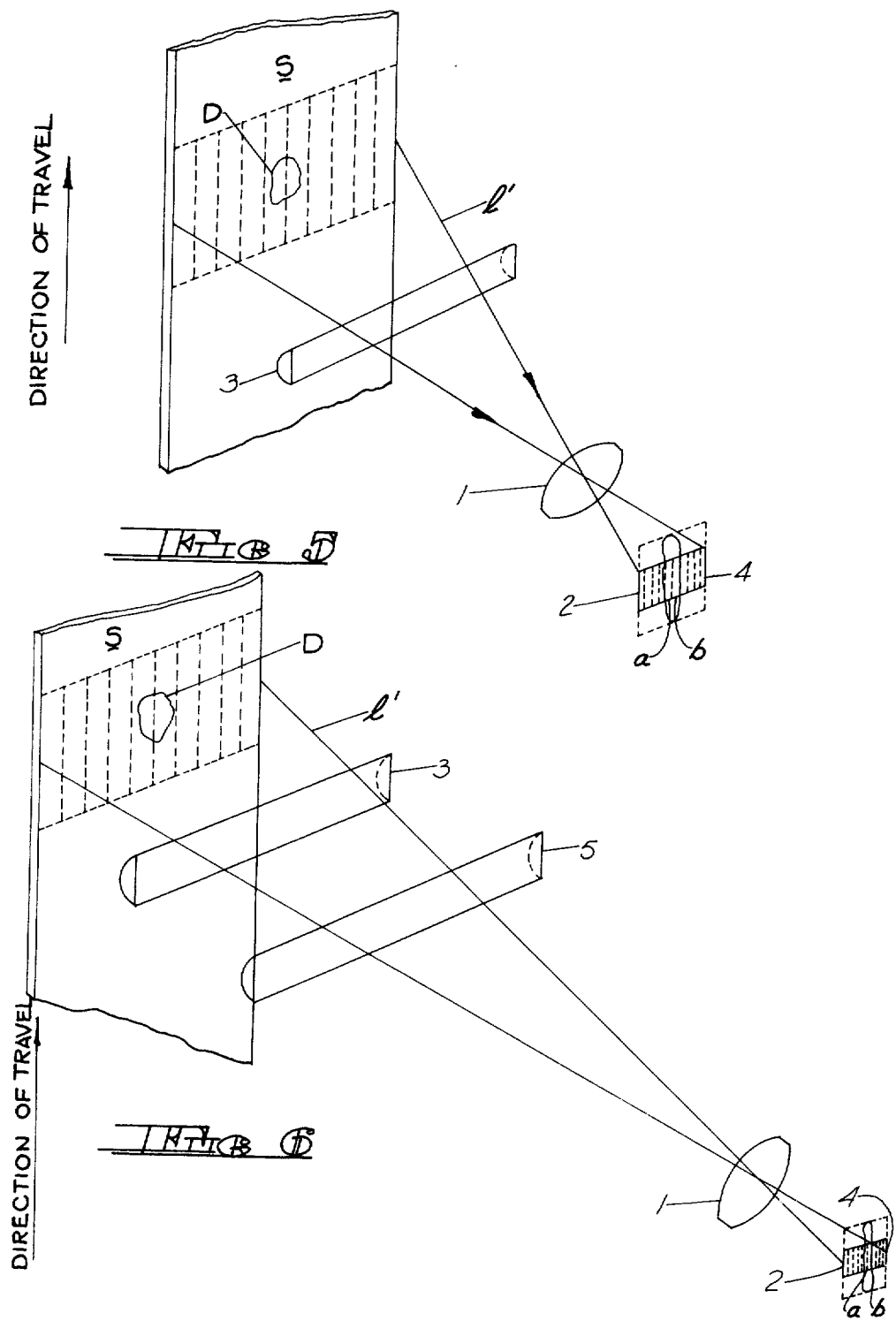

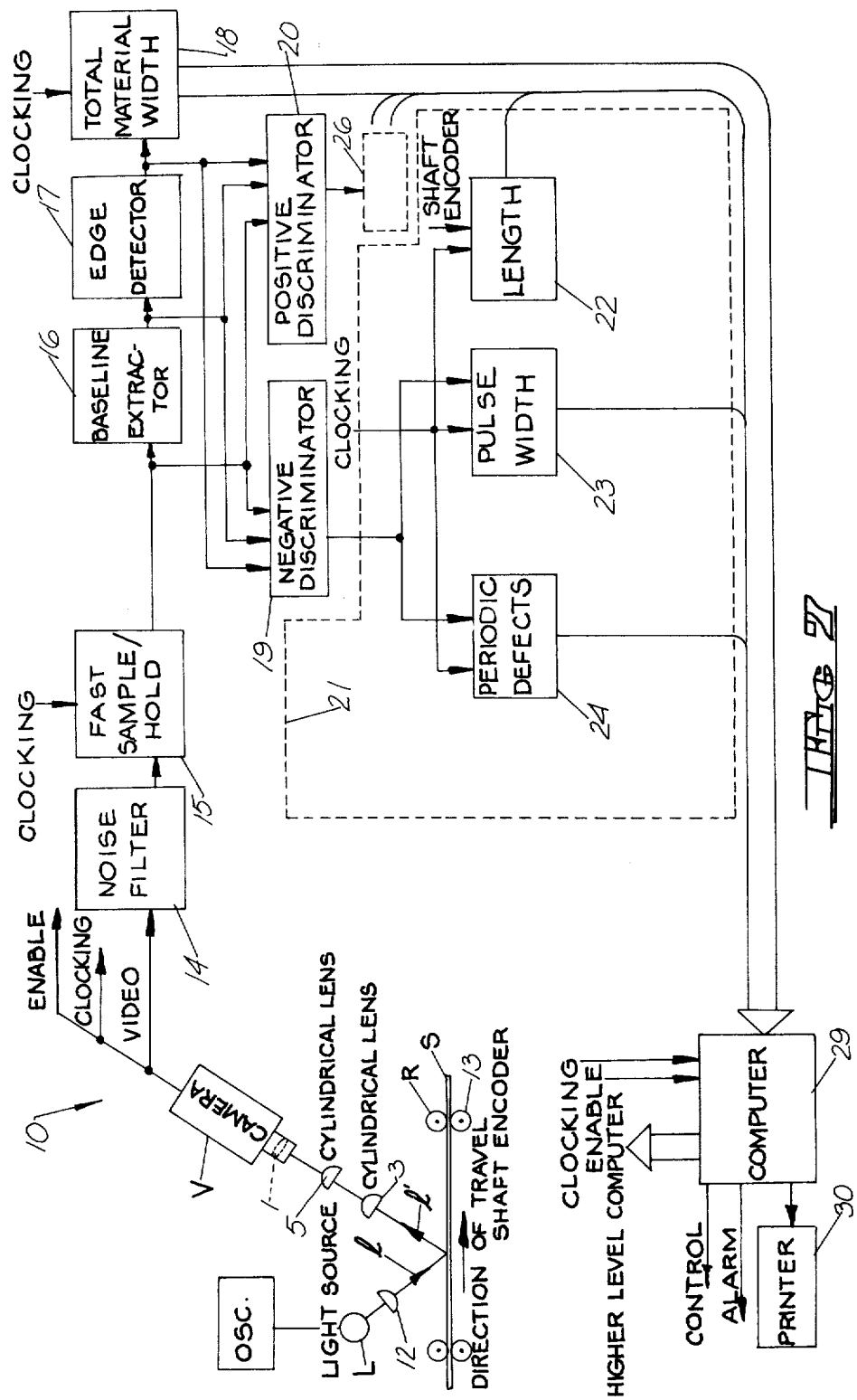

AUTOMATIC DEFECT DETECTING INSPECTION APPARATUS

BRIEF SUMMARY OF THE INVENTION

The continuous inspection of semi-finished material during continuous fabrication or manufacturing processing is a critical step in assuring that the end product is free from defects or imperfections. Often these defects, if seasonably detected and classified, can be excised or repaired before the semi-finished material moves on to a subsequent processing station. One particular area where defect detection has been an important concern is in the processing and inspection of metallic slabs or sheet material, where the imperfections may appear as perforations, cracks, indentations, included material, etc. When light is reflected from the surface of the material, these imperfections may exhibit an optical appearance different from the remainder of the surface as the result of light reflected or absorbed by the defect. If the material is heated, such as in the case of hot steel slabs, for example, the defects may appear as darker or lighter areas, depending upon the relative emitted radiation.

In any event, it has been found that the apparent difference in appearance between such defects and the surrounding surface of the material is such that the defects can be detected and classified by mere visual inspection in many cases. This is particularly the case if the material is moving at a relatively slow speed permitting a human observer to easily inspect the surface for imperfections. In some instances, the observer need not be physically present at the inspection station so that a visual image of the material surface may be transmitted to a distant location where an observer can monitor conditions at one or more inspection stations. Such a technique is illustrated in U.S. Pat. No. 3,176,306 issued Mar. 30, 1965 to Charles Burns.

However, as the speed of the material past the inspection station is increased, it becomes increasingly difficult for a human observer to visually discern defects or imperfections appearing on the surface of the rapidly moving material. In response to this need, prior art workers have developed several different techniques for automatically detecting defects in rapidly moving sheet or sheet-like material. An exemplary automatic inspection technique of this type is disclosed in U.S. Pat. No. 3,096,443 issued July 2, 1963 to John F. Laycak.

In this arrangement, the surface of the strip or slab to be inspected is illuminated by a suitable light source. A vidicon is positioned to receive light from the light source reflected by the surface of the strip or slab, so that the surface of the strip or slab is scanned by the vidicon in a direction substantially transverse to the direction of travel of the material. Defects appearing on the surface of the material will have a differing reflectivity and thus appear darker or lighter. If the material being inspected is raised to an elevated temperature, and consequently is irradiant, defects on its surface will appear brighter or darker than the remainder of the material. In either event, the vidicon will produce a video signal containing pulses having pulse widths proportional to the width of the defect appearing on the surface of the strip or slab. These pulses, as well as information reflecting the speed and physical dimensions of the strip of slab, may thereafter be processed to provide information concerning the size, position, characteristic, or frequency of occurrence of defects.

While vidicon camera surface inspection systems have proven, in general, adequate to detect defects appearing on moving sheet or slabs, there are certain limitations. A relatively new type of sensor has a number of advantages that make it superior to the vidicon for use in an automatic surface inspection system. This sensor is the linear solid state charge transfer device (e.g. silicon charge coupled array, silicon photodiode array). The array contains a line of tiny (e.g. 25 micron by 25 micron) individual light sensing elements placed side-by-side. These elements are accessed electronically to produce a serial voltage output characteristic of the light which has fallen on each element from a particular location on the surface which has been focused on the array. An example of the use of such an array in a flaw detection system may be found in U.S. Pat. No. 3,877,821 issued Apr. 15, 1975 to Stephen E. Price, et al. The advantages of the solid state linear array over the vidicon include no image lag at high scan rates, no image "burn-in" at high light levels, improved blooming characteristics, very accurate positional information concerning flaw locations on the object being scanned as a result of the fixed geometry of the photosensors, lower system noise and higher signal to noise ratio at higher light levels, low operating voltages, longer lifetime, and built-in clock for synchronizing further digital processing of defect information. The present invention relates to a method for further improving the characteristics of the self-scanned array camera over the vidicon by improving sensitivity to defects transverse to the scanned line of the array.

In general, the optics usually employed with the vidicon comprise a simple converging lens which magnifies equally both dimensions of a two dimensional image plane. While this feature is desirable for television applications, for example, where an equally magnified undistorted image is desirable, it is unacceptable for defect detection applications. This is due to the fact that equal magnification in both dimensions or meridians of the image plane limits the sensitivity of a line-scan camera to short defects having a dimension small in length in the direction of material travel. Consequently, if it is desired to inspect a given width of material, a camera lens having the appropriate magnification for the desired focal length can be chosen such that the material width can just be focused on the photo sensitive array. Once this field of view width has been chosen, the length of the field of view is fixed. Since the ability to detect a given defect will be determined by the percentage of the field of view occupied by the defect, defects having a relatively short dimension in the direction of material travel may not be detected.

The present invention overcomes these problems by decoupling the length of the field of view from the width of the field of view by introducing an anamorphic optical system such as a cylindrical lens or lenses between the moving material and the camera lens. The cylindrical lens is oriented so that the length of the field of view is magnified without affecting the width of the field of view. Hence, the image of the defect focused on the photo sensitive array of the camera will occupy a larger percentage of the photo sensitive array due to the magnified length of the defect. In this way, it is possible to obtain improved sensitivity to defects having a relatively short length within the limits imposed by specific material widths.

Further features of the invention will become apparent from the detailed description which follows.

BRIEF DESCRIPTION OF THE DRAWING

FIG. 5 illustrates diagramatically the imaging arrangement of the defect detection system of FIG. 4.

FIG. 6 diagramatically illustrates the imaging arrangement of the defect detection system of FIG. 4 using two cylindrical lenses.

FIG. 7 is an operational block diagram of a preferred embodiment of the defect detection system of the present invention.

DETAILED DESCRIPTION

Figure 1:
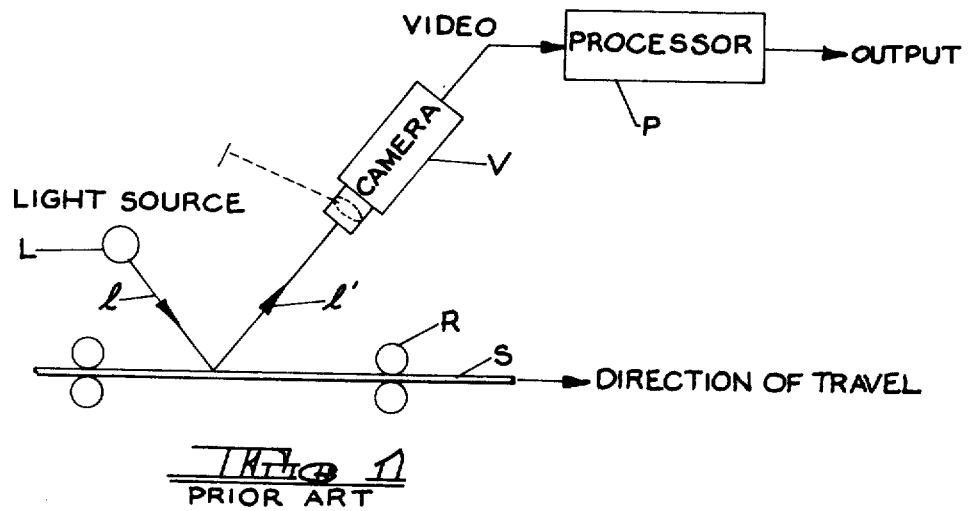
FIG. 1 is a diagramatic illustration of a typical prior art defect detection system.

FIG. 1 illustrates diagramatically a typical prior art automatic defect detecting inspection system for analyzing defects or imperfections in or on a moving strip or slab S. In general, strip or slab S, which may be of any desired width or length, is supported and guided by guide rollers, one of which is designated R, in the direction shown, so that strip or slab S passes beneath the inspection station at a relatively constant speed.

In some applications where the strip or slab S material is heated, such as in the case of hot steel slabs, for example, the surface of the material will be irradiant, causing the defects to appear as darker or lighter areas, depending upon the relative emitted radiation. In other situations, such as that illustrated in FIG. 1, an external light source L may be necessary to illuminate the surface of the moving strip or slab S. In many situations, such as that described in U.S. Pat. No. 3,096,443, light source L may be a linear light source such as florescent lamp or the like which directs a narrow beam of light onto the surface of the strip or slab S along a path extending substantially perpendicular to the direction of movement. Focusing optics may also be included between light source L and the surface of the moving material to further concentrate and collimate the light so as to produce a clearly defined area of illumination.

Some of the light rays 1 directed toward the surface of the moving strip or slab S are absorbed or scattered by the material or defects appearing on or within the material. The remaining rays 1' are reflected in a direction toward an optically sensitive device V, which may be a vidicon camera as is well understood in the art.

Vidicon camera V scans the surface of the moving material within an area specified by the lens parameters and vidicon tube dimensions. Defects appearing on the surface of the material and having a lower or higher reflectivity causing them to appear darker or lighter, respectively, will cause the vidicon camera V to produce a video signal containing pulses having pulse widths proportional to the width of the defect appearing on the surface of the strip or slab S. This video information, as well as other information reflecting the speed and physical dimensions of the strip or slab, may thereafter be processed in processor P to provide output information concerning the size, position, characteristic, or frequency of occurrence of defects or imperfections.

Figure 3:
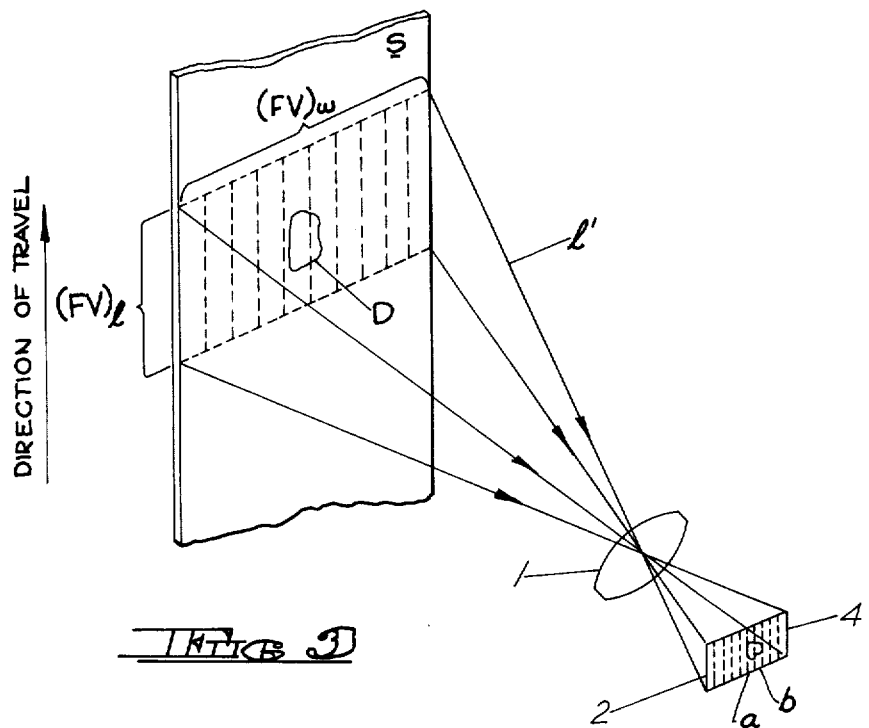
FIG. 3 is a diagramatic illustration of the imaging arrangement of the present invention.

The performance of the defect detection system of the present invention provides improved performance by employing a photo sensitive array 2 consisting of a number of separate photo detector elements, one of which is shown at 4 in FIG. 3. Such an arrangement is significantly different from the construction utilized in a typical vidicon, for example, which contains a single photoconductive screen which is accessed by a scanned electron beam. The active sensing area 2 illustrated in FIG. 3 utilizes a plurality of individual light sensing elements 4 placed side-by-side to form a light sensitive matrix, the individual elements 4 being accessed in such a way so as to produce a serial output signal characteristic of the light which has fallen on a particular element from a particular location on the moving material. An example of the use of a similar type of array may be found in U.S. Pat. No. 3,877,821 issued Apr. 15, 1975 to Stephen E. Price et al. It will be understood that this arrangement allows accurate defect width measurements by merely counting the number of elements 4 that exceed a given threshold and then multiplying this number by the real space resolution of each element. Furthermore, by noting the particular elements covered by the defect, an accurate determination of the position of the defect within the field of view may be determined. For example, in FIG. 3 it is noted that defect D covers portions of elements a and b indicating that the defect has occurred approximately in the center of strip or slab S.

Figure 2:
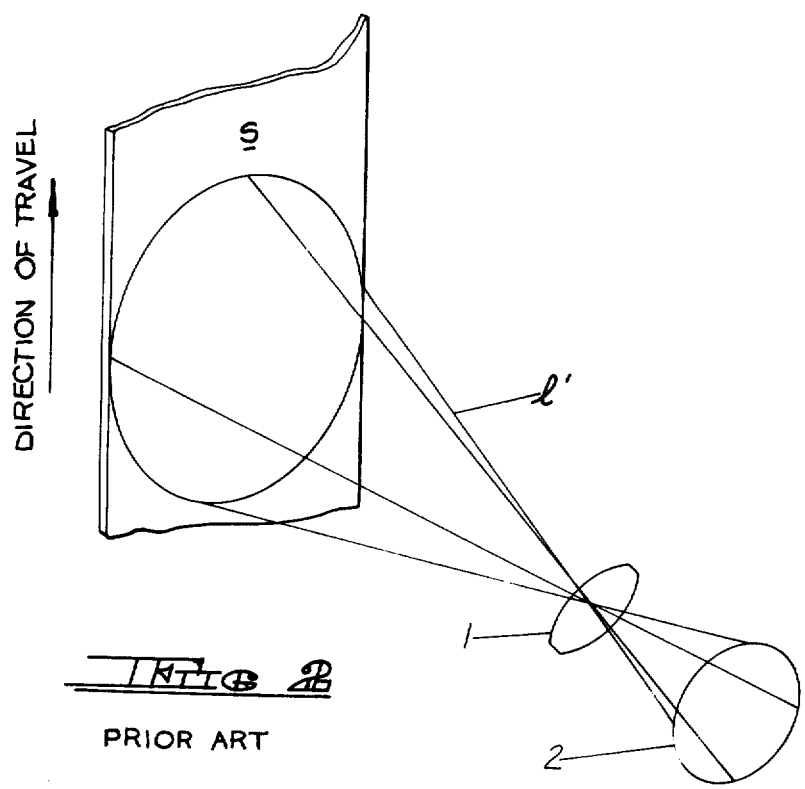
FIG. 2 is a diagramatic illustration of the imaging arrangement of a typical prior art defect detection system.

As is well understood in the art, optically sensitive devices such as vidicon cameras or solid state line-scan cameras which have been heretofore employed in defect detection and inspection systems contain optics comprising one or more lenses which magnify equally both dimensions of a two-dimensional image plane, as illustrated in the conventional optical arrangement of FIG. 2. In such an arrangement, it is generally preferred that the simple converging lens optics 1 of the camera V be located a predetermined distance from the surface of strip or slab S such that light rays 1' reflected from the surface of the material will exactly fill the active sensing area 2 of the camera V. As is well understood in the art, the location of lens 1 with respect to strip or slab S and active sensing area 2 will depend upon the field of view desired as well as the focal length of the lens. In defect detection and inspection applications, the width field of view, commonly designated $(FV)_w$, will generally be chosen to encompass the entire width of the strip or slab S material, while the length field of view, commonly designated $(FV)_l$ will generally be chosen to encompass a length of the moving strip or slab S material corresponding to the length of the smallest defect which the system is capable of resolving. In order to insure optimum sensitivity, this field of view $(FV)_w \times (FV)_l$ must exactly fill the active sensing area 2 when focused through converging lens 1. Active sensing area 2 will generally be rectangular and have an array width (AW) aligned perpendicular to the direction of strip or slab travel, and an array length (AL) aligned in the direction of strip or slab travel. As is well known in the art, the magnification of converging lens 1 is related to the field of view and active sensing area by means of the relationship:

$$M = (AL)/(FV)_l = (AW)/(FV)_w$$

In other words, the magnification is the maximum image length or length of the sensing element (AL) divided by the maximum object length which can just be focused on this array $(FV)_l$. Since the camera lens 1 is a two dimensional magnification device, this same magnification M equals the maximum image width or width of the sensing element (AW) divided by the maximum object width which is focused on the array or the corresponding maximum width of the field of view that can just be focused on this array $(FV)_w$. Hence, a rectangular-shaped array will result in a rectangular-shaped field of view, since the array dimensions can be visualized as being projected backwardly onto the object by the camera lens.

It is to be noted from these relationships that once an array of fixed dimensions is chosen, the camera lens focal length and distance to the object determine the dimensions of the field of view that are sensed by the array. The lens magnification is determined by the width of material to be scanned. The distance from the lens to the object is then adjusted to exactly fill the width of the array with this object dimension for the particular lens focal length. Since the length of the field of view $(FV)_l$ is determined by the choice of the width of the field of view $(FV)_w$, a defect or imperfection having a length equivalent to a small percentage of the length of the field of view may not be detected, since the amount of light reflected from the segment of the field of view occupied by the defect or imperfection may not be sufficiently different from the light reflected from adjacent non-defective segments of the moving material.

Figure 4:
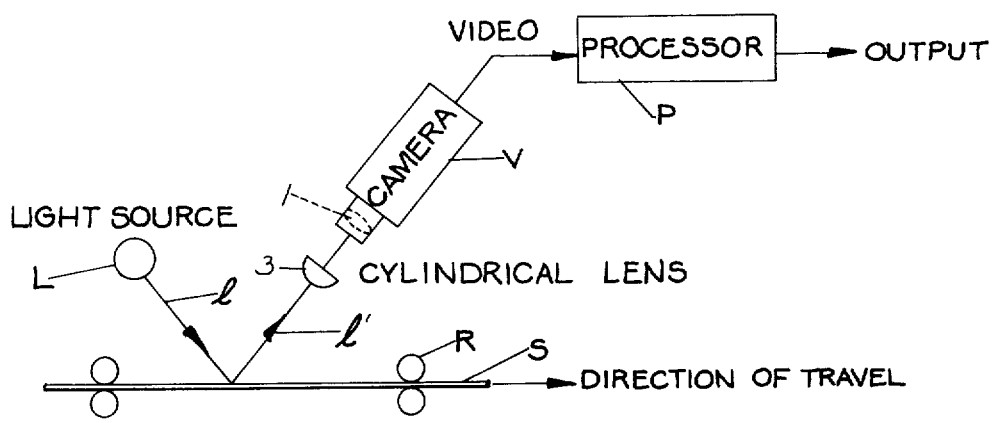
FIG. 4 is a diagramatic illustration of the defect detection system of the present invention including a single cylindrical lens.

The present invention provides a significant improvement in the sensitivity or signal to noise ratio of known automatic inspection or defect detection systems by decoupling the length of the field of view from the width of the field of view by introducing an anamorphic optical system between the moving material and the camera lens as illustrated in FIG. 4. In the preferred embodiment illustrated in FIG. 4, a cylindrical lens 3 is positioned to capture light rays 1' reflected from the surface of moving strip or slab S, and is so oriented that it magnifies the length of the field of view while not affecting the width of the field of view. Hence, the image of the defect focused on photo sensitive array 2 will occupy a larger percentage of the photo sensitive array due to the magnified length of the defect. In this way, it is possible to obtain improved sensitivity to defects having a relatively short length within the limits imposed by specific material widths. While for purposes of an exemplary showing, the automatic inspection and defect detection system in the present invention has been described as utilizing an anamorphic optical system comprising a cylindrical lens, it is considered to be within the purview of the present invention to include anamorphic optical systems having prisms and the like as well. Furthermore, lens 3 may be a single convex cylindrical lens as illustrated, or other configurations such as double convex, etc.

In some situations, it may be found that the cylindrical lens 3 chosen has a short focal length requiring that lens 3 be positioned close to moving strip or slab S, which may not be desirable in some applications. Under these circumstances, the arrangement of FIG. 6 may be advantageously employed where a second cylindrical lens 5 is positioned between cylindrical lens 3 and simple converging lens 1 to form a simple Galilean telescope. In general, the real image formed by the first cylindrical lens 3 is made to occur just inside the primary focal point of the second lens 5 so that a magnified virtual image is obtained for focusing by converging lens 1. Thus, the system has a magnification equal to that of the converging lens 1 in a direction perpendicular to the direction of travel of strip or slab S, and a magnification equal to the product of the magnification of the cylindrical telescope and converging lens 1 in the direction parallel to the direction of travel of strip or slab S. Hence, cylindrical lenses 3 and 5 may be positioned at a greater distance from the moving material, while maintaining the same magnification in the direction of the length of defects appearing on the surface of the material in order to obtain a satisfactory signal to noise ratio. It will be understood that the magnification of the cylindrical telescope formed by cylindrical lenses 3 and 5 will be chosen so that the shortest defects of interest are magnified sufficiently to entirely fill the length of one or more elements 4 within array 2. The length of cylindrical lenses 3 and 5 will generally be determined by the width of the strip or slab S to be inspected, as well as the distances of the cylindrical lenses from the strip or slab.

FIG. 7 illustrates a preferred embodiment of the automatic inspection and defect detection system of the present invention, shown generally at 10, utilizing the novel cylindrical lens features described hereinabove.

Illumination from strip or slab S is provided by light source L, which may be a linear light source such as a florescent lamp or the like which directs a narrow beam of light onto the surface of strip or slab S along a path extending substantially perpendicular to the direction of movement. In order to remove flicker from the output of lamp L, the lamp may be driven at a relatively high frequency, for example 40 kilohertz, by means of power oscillator 11. For very high scan rates, a high intensity constant output source such as a tungsten filament lamp may be employed. Light rays 1 produced by lamp source L may be further concentrated or collimated onto the surface of moving strip or slab S by means of a cylindrical lens 12, or other suitable optics.

As described hereinabove, strip or slab S is supported and guided by guide rollers, one of which is designated R, in the direction shown, so that the strip or slab S passes beneath the inspection station at a relatively constant speed. A tachometer or shaft encoder 13 may be attached to one of the guide rollers R to provide an output signal proportional to the speed of slab or strip S. This information will be utilized as explained in more detail hereinafter to determine the length position of a defect occuring on the surface of the moving material.

Light rays 1' reflected from the surface of the moving material are directed through a cylindrical telescope consisting of cylindrical lens 3 and cylindrical lens 5 to objective converging lens 1 of camera V as described hereinbefore. In a preferred embodiment, camera V will be of the type having a sensing element comprised of a plurality of separate adjacent photodetector elements which are serially scanned to produce an output VIDEO signal varying in response to light reflected from the surface of moving slab or strip S as the surface of the moving material is scanned by camera V along a line extending substantially perpendicular to the direction of movement of the material. Hence, defects having a higher reflectivity than the surrounding area of the material will produce positive-going pulses having a pulse width proportional to the width of the defect measured in a direction perpendicular to the direction of travel of the material. Conversely, defects having a reflectivity less than that of the surrounding material will produce negative-going pulses also having widths corresponding to the width of the defect as measured in a direction perpendicular to the direction of travel of the material. Since the cylindrical lens system described hereinabove tends to stretch or elongate the actual image of the defect in a direction parallel to the direction of travel of the material, a defect may be scanned several times by camera V. Consequently, the novel optical means of the present invention positioned between the moving material and the optically sensitive device V increases the sensitivity of the optically sensitive device in the direction of material travel.

Camera V may also produce CLOCKING signals which serially interrogate each photo sensitive element 4 in the scanning array to produce the VIDEO signal reflecting the amount of light striking that particular element 4. ENABLE signals are also produced by camera V to provide indication when the photodiodes are being accessed.

The VIDEO signal output produced by camera V is processed by noise filter 14 which removes high frequency clocking noise components from the VIDEO signal. The resulting filtered VIDEO signal together with the CLOCKING signal are provided as inputs to fast sample/hold circuit 15 which also operates to reduce CLOCKING noise by establishing the magnitude of each VIDEO pulse at a level corresponding to the relatively constant amplitude of the pulse following the unstable forward edge pulse transition.

The base line extractor circuit 16 eliminates signals caused by background energy in order to make the sensitivity of the system uniform across the entire width of the material. This feature is particularly important in applications where the reflectivity may not be constant across the material width, such as where a light stain may be present on the surface of the material. In a preferred embodiment, baseline extractor circuit 16 filters the VIDEO signal to remove the slower time-varying background signal. A constant, which may be fixed or dependent upon a calculated main value background signal, is substracted from the VIDEO signal. Such processing is well-known in the art, and need not be described in detail.

Edge detector circuit 17 compares a fixed voltage level with the processed VIDEO signal in order to provide a digital output signal having a width corresponding to the width of the material being scanned. That is, an output pulse will be produced from edge detector circuit 17 whenever the processed VIDEO signal exceeds the preset threshold value. The total material width circuit 18 counts the number of CLOCKING pulses occurring during the output signal from edge detector circuit 17 in order to provide a relative measure of the width of the material being examined.

Processed VIDEO pulses from the base line extractor circuit and edge detector circuit are operated on by negative discriminator 19 which produces a digital output pulse having a width corresponding to the width of negative-going VIDEO pulses, which correspond to decreases in light reflected from the surface of the moving strip or slab S. A similar positive discriminator circuit 20 produces digital output pulses having pulse widths corresponding to positive-going VIDEO signals. The resulting output signals from negative discriminator 19 are processed by processing circuit 21, which comprises length detector 22, pulse width detector 23, and periodic defect detector 24. It will be understood that in the description to follow, similar processing takes place in processor 26 upon positive discriminator pulse outputs from positive discriminator 20.

In the preferred embodiment shown in FIG. 7, length detector 22 utilizes positional information from shaft encoder 13 for each defect, so that defects can be catagorized according to length. Pulse width detector 23 classifies the detected defects using pulse width as the criteria by noting the number of VIDEO elements covered by the particular defect. Periodic defect detector 24 classifies defects caused by periodic perturbations such as might be caused by periodic burnish marks, holes, dents, gouges, etc. Each of the aforementioned processing and classifying processors is well-known in the art and need not be described in detail.

The resulting output signals from total material width circuit 18, processor 21, and processor 26, together with CLOCKING and ENABLE signals, are sent to computer 29 which tabulates the information concerning defect occurrence, distribution and location. For example, computer 29 can be utilized to rate the surface of the strip on slab based on total defective surface area. Alternatively, the specific position of each defect may be noted and a written record of such occurrences provided by printer 30, or the defect positional information utilized to alert the operator that a defect has occurred via the ALARM signal, or the information used to automatically control peripheral defect treating equipment (not shown) such as scarfers, etc. The data tabulated by computer 29 may also be used to control a higher level computer overseeing the operation of a plurality of defect detection systems, for example.

It will be understood that various changes in the details, materials, steps and arrangements of parts, which have been hereindescribed and illustrated in order to explain the nature of the invention, may be made by those skilled in the art within the principal and scope of the invention as expressed in the appended claims.

The embodiments of the invention in which an exclusive property or privilege is claimed are as follows:

1. Automatic defect detecting apparatus for inspecting and detecting defects on the surface of a moving sheet of material, said defects having a visual appearance different from the remainder of said sheet surface, said apparatus comprising a light source for illuminating a selected portion of said sheet surface, means for scanning said selected portion of said sheet in a direction transverse to the direction of sheet movement to produce an output video signal corresponding to the optical intensity of the area scanned, means for processing said output video signal to produce information characterizing the nature of the optical intensity of said area scanned, and optical means positioned between the moving sheet of material and said scanning means for increasing the sensitivity of said scanning means in the direction of material movement while maintaining the sensitivity of said scanning means substantially unchanged in the direction transverse to material movement.

2. The apparatus according to claim 1 wherein said light source comprises a linear light source.

3. The apparatus according to claim 2 including means for exciting said linear light source at a frequency substantially higher than the scan rate of said scanning means.

4. The apparatus according to claim 1 wherein said scanning means comprises an array of optically sensitive elements arranged in side-by-side relationship, the total width of said array corresponding to the field of view of said optical means in a direction transverse to material movement, said elements being accessed sequentially to produce a serial train of video pulses comprising said output video signal, each of said pulses corresponding to the output from a single element.

5. The apparatus according to claim 1 wherein said optical means comprises an anamorphic optical system.

6. The apparatus according to claim 5 wherein said optical means comprises a first cylindrical lens having a length field of view corresponding to the width of said sheet of material.

7. The apparatus according to claim 5 wherein said first cylindrical lens comprises a double convex lens.

8. The apparatus according to claim 5 wherein said optical means includes a second cylindrical lens positioned between said material and said first cylindrical lens, said lenses forming a Galilean telescope.

* * * * *